(12) United States Patent
Lubin et al.

(10) Patent No.: US 11,969,214 B1
(45) Date of Patent: Apr. 30, 2024

(54) RETINAL CAMERAS HAVING MOVABLE OPTICAL ASSEMBLIES FOR FACILITATING MULTI-STAGE RETINAL IMAGING

(71) Applicant: Verily Life Sciences LLC, Mountain View, CA (US)

(72) Inventors: James K. Lubin, Mountain View, CA (US); Ryan Kramer, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 761 days.

(21) Appl. No.: 17/077,279

(22) Filed: Oct. 22, 2020

Related U.S. Application Data

(60) Provisional application No. 62/924,512, filed on Oct. 22, 2019.

(51) Int. Cl.
*A61B 3/15* (2006.01)
*A61B 3/12* (2006.01)

(52) U.S. Cl.
CPC ................ *A61B 3/152* (2013.01); *A61B 3/12* (2013.01)

(58) Field of Classification Search
CPC .................................. A61B 3/152; A61B 3/12
USPC ...................................................... 351/206
See application file for complete search history.

(56) References Cited

U.S. PATENT DOCUMENTS

| 5,943,122 | A | * | 8/1999 | Holmes | G01J 3/4535 356/73 |
|---|---|---|---|---|---|
| 7,338,167 | B2 | | 3/2008 | Zelvin et al. | |
| 8,550,624 | B2 | * | 10/2013 | Padrick | A61B 3/152 351/200 |
| 2006/0268230 | A1 | | 11/2006 | Kogawa et al. | |
| 2015/0042951 | A1 | * | 2/2015 | Stanga | A61B 3/12 351/206 |
| 2017/0176338 | A1 | * | 6/2017 | Wu | G01N 21/6428 |
| 2019/0154439 | A1 | * | 5/2019 | Binder | G01B 11/26 |

FOREIGN PATENT DOCUMENTS

| CN | 109793495 A | 5/2019 |
|---|---|---|
| JP | 3753855 B2 | 12/2005 |

* cited by examiner

*Primary Examiner* — Mohammed A Hasan
(74) *Attorney, Agent, or Firm* — Perkins Coie LLP

(57) ABSTRACT

Introduced here are retinal cameras having one or more optical components whose position can be modified so that the left and right eyes can be imaged during a single imaging operation. Collectively, the optical component(s) may be referred to as an "optical assembly." An optical assembly can include the objective lens, lens tube, and other optical components such as mirror(s), light source(s), capturing medium(s), etc. An optical assembly of a retinal camera may be movable between a first position and a second position along an arcuate path. By moving the optical assembly between the first and second positions along the arcuate path, the retinal camera can align the lens tube with the left and right eyes of an individual while clearing her nose. Thus, the retinal camera may generate images of the left and right eyes during an imaging procedure without requiring that the individual move her head.

19 Claims, 13 Drawing Sheets

RETINAL CAMERAS HAVING MOVABLE OPTICAL ASSEMBLIES FOR FACILITATING MULTI-STAGE RETINAL IMAGING

CROSS-REFERENCE TO RELATED APPLICATIONS

This application claims priority to U.S. Provisional Application No. 62/924,512, filed on Oct. 22, 2019, which is incorporated by reference herein in its entirety.

TECHNICAL FIELD

Various embodiments concern retinal cameras having movable optical assemblies.

BACKGROUND

Fundus photography involves capturing an image of the fundus (i.e., the interior surface of the eye opposite the lens) to document the retina, which is the neurosensory tissue in the eye that translates optical images into the electrical impulses that can be understood by the brain. The fundus can include the retina, optic disc, macula, fovea, and posterior pole.

Retinal cameras (also referred to as "fundus cameras") typically include a microscope and a capturing medium that creates an image from light reflected by the retina. Because the pupil serves as both the entrance point and exit point of light guided toward the retina, the retina can be photographed directly. The structural features that can be identified in a retinal image include the central and peripheral retina, optic disc, and macula.

Medical professionals, such as optometrists, ophthalmologists, and orthoptists, can use retinal images to monitor the progression of diseases and eye conditions. For example, retinal images may be used to document indicators of diabetes, age-macular degeneration (AMD), glaucoma, neoplasm, etc.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

Figure 1:
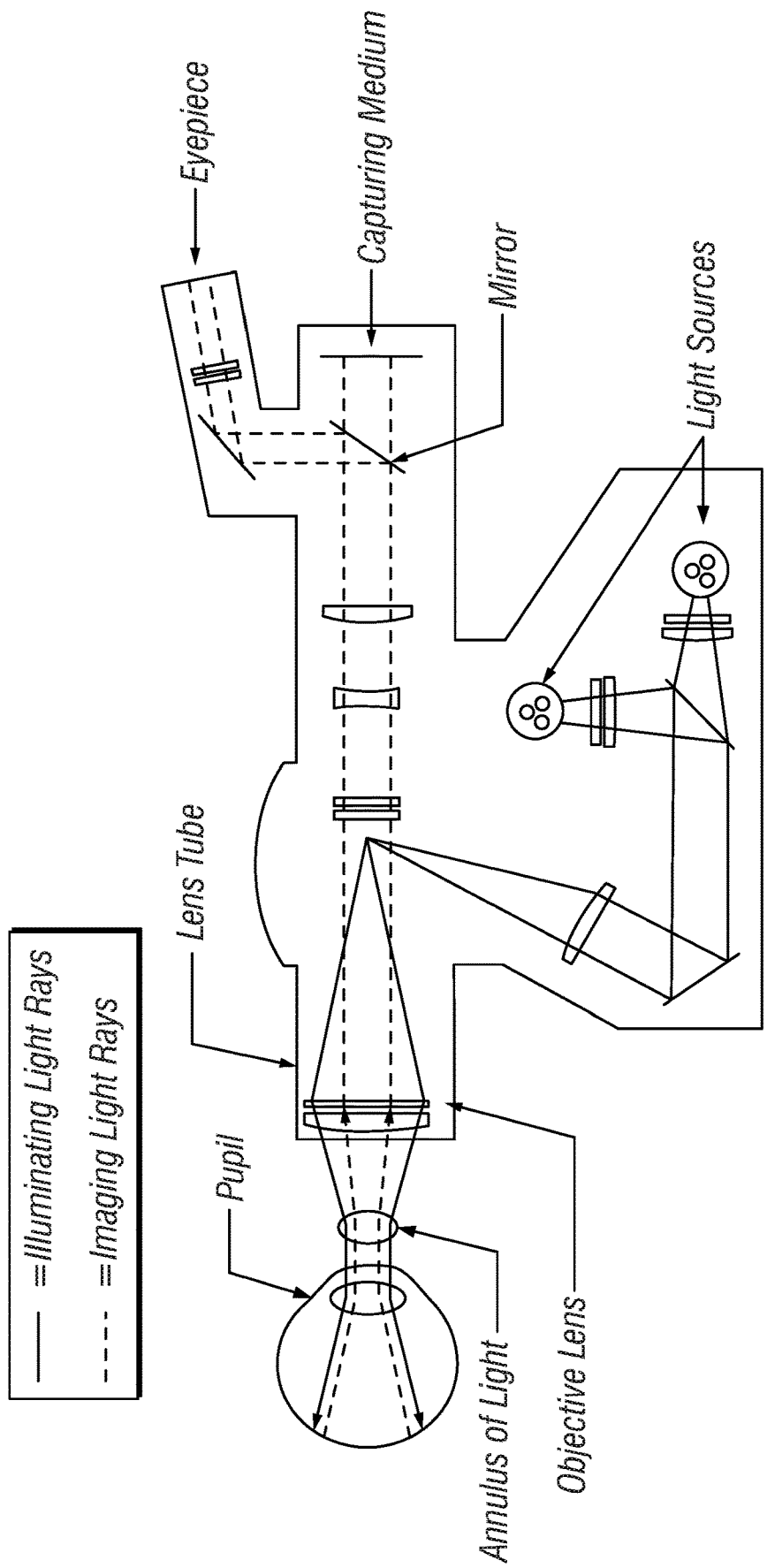
FIG. 1 depicts an example of a conventional retinal camera.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Retinal cameras are designed to provide an upright, magnified view of the fundus. Typically, a retinal camera views approximately 30-50° of the retinal area with a magnification of 2.5×, though these values may be modified using zoom lenses, auxiliary lenses, wide-angle lenses, etc.

FIG. 1 depicts an example of a conventional retinal camera. Generally, a subject (also referred to as a "patient") will sit at the retinal camera with her chin set within a chin rest and forehead pressed against a bar. An ophthalmic photographer can then visually align the objective lens of the retinal camera (e.g., using an eyepiece) and press a shutter release that causes an image of the retina to be captured. The ophthalmic photographer may be the medical professional responsible for examining the image or some other individual.

In particular, FIG. 1 illustrates how light can be focused via a series of lenses to form an annulus that passes through the objective lens located at the end of a lens tube and onto the retina. The illuminating light rays are generated by one or more light sources (e.g., light-emitting diodes), each of which is electrically coupled to a power source. When the retina and the objective lens are aligned, light reflected by the retina passes through the unilluminated hole in the annulus toward the objective lens. Those skilled in the art will recognize that the optics of the retinal camera are similar to those of an indirect ophthalmoscope in that the illuminating light rays entering the eye and the imaging light rays exiting the eye follow dissimilar paths.

Initially, the imaging light rays exiting the eye can be guided toward an eyepiece that is used by the ophthalmic photographer to assist in aligning/focusing the illuminating light rays. When the ophthalmic photographer presses the shutter release, a first mirror can interrupt the path of the illuminating light rays and a second mirror can fall in front of the eyepiece. Such action causes the imaging light rays to be redirected onto a capturing medium. Examples of capturing mediums include film, digital charge-coupled devices (CCDs), and complementary metal-oxide-semiconductors (CMOSs). In some embodiments, retinal images are captured using colored filters or specialized dyes (e.g., fluorescein or indocyanine green).

Stable alignment of the eye and the objective lens located at the end of the lens tube is key to capturing high-resolution retinal images. To capture a high-resolution retinal image, the lens tube must be precisely aligned with the eye—usually within a tolerance of several millimeters. However, initiating such an alignment in preparation for an imaging procedure can be challenging, especially if both eyes must be imaged, in which case the lens tube of the retinal camera must be shifted from one eye to the other eye over the course of the imaging procedure.

Introduced here, therefore, are retinal cameras having one or more optical components whose position can be modified so that the left and right eyes can be imaged during a single imaging operation. Collectively, the optical component(s) may be referred to as an "optical assembly." As further discussed below, an optical assembly can include the objective lens, lens tube, and other optical components such as mirror(s), light source(s), capturing medium(s), etc.

An optical assembly of a retinal camera may be movable between a first position and a second position along an arcuate path. By moving the optical assembly between the first and second positions along the arcuate path, the retinal camera can align the lens tube with the left and right eyes of an individual while clearing her nose. For instance, the lens tube may initially be moved away from the left eye, swung toward the right eye along the arcuate path, and then moved toward the right eye.

This stands in contrast to conventional retina cameras in which the lens tube is manually aligned with each eye. There are three different types of conventional retinal cameras:

Desktop retinal cameras with movable optical assemblies designed for alignment with an eye after a subject has placed her chin in a chin rest. After an image of an eye has been generated, an optical assembly can be moved to align with the other eye. While the optical assembly is normally moved by an operator using a joystick or some other control mechanism, the optical assembly could be automatically moved along a substantially linear track using, for example, a three-axis motor stage.

Desktop retinal cameras with fixed optical assemblies with which the subject will align an eye. After an image of the eye has been generated, the subject can reposition her head with respect to an optical assembly in order to generate an image of the other eye. Because the subject is responsible for repositioning her head during an imaging operation, proper alignment can be difficult to achieve.

Handheld retinal cameras that require an operator responsible for manually aligning the optical assembly with each eye during an imaging procedure. Retinal images generated by handheld retinal cameras often have poor quality due to the inherent instability of manual alignment.

For the reasons discussed above, it can be difficult to consistently produce high-quality retinal images of the left and right eye during a single imaging procedure with these conventional retina cameras. The retinal cameras described herein, however, include optical assemblies whose position can be modified during an imaging operation in order to generate images of the left and right eye without requiring the subject move her head. Instead, the subject can place her head against a flexible mask designed to envelop the left and right eyes, and then the optical assembly of the retinal assembly can be moved, either manually or automatically, between multiple positions in order to generate images of the left and right eyes.

Embodiments may be described with reference to particular control mechanisms, lens configurations, etc. However, those skilled in the art will recognize that the features described herein are equally applicable to other control mechanisms, lens configurations, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for aligning the lens tube of a retinal camera with a first eye, determining that a first image of the first eye has been generated, moving the lens tube to be aligned with a second eye, causing a second image of the second eye to be generated, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here.

Similarly, steps could be replaced or reordered. Thus, descriptions of any processes are intended to be open-ended.

Arcuate Path for Movement of Optical Assembly

Figure 2:
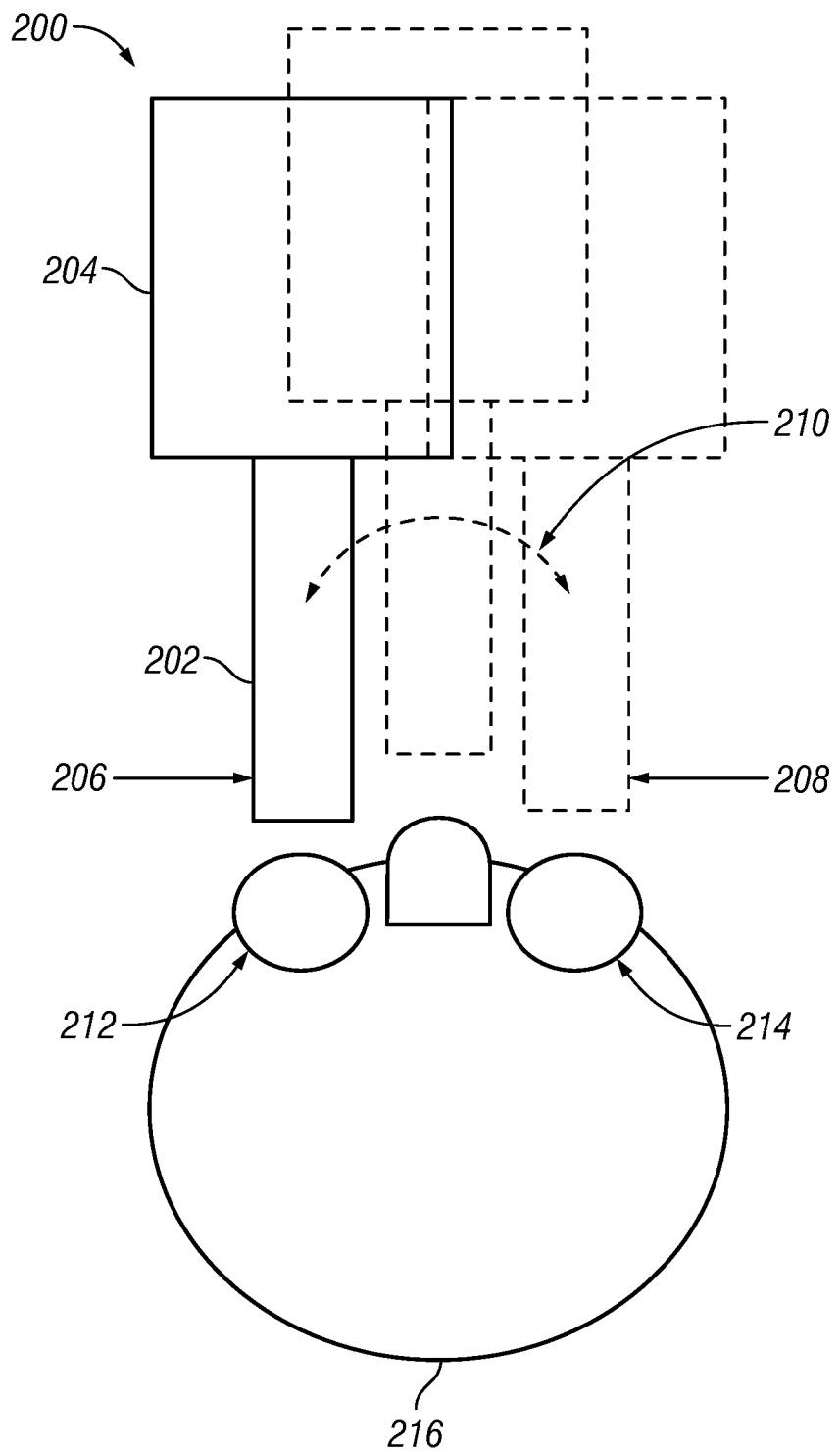
FIG. 2 illustrates how at least some of the optical components included in a retinal camera may be moved during an imaging procedure in order to seamlessly generate images of both eyes.

FIG. 2 illustrates how at least some of the optical components included in a retinal camera may be moved during an imaging procedure in order to seamlessly generate images of both eyes. The optical components may be collectively referred to as an optical assembly 200. Here, the optical assembly 200 includes a lens tube 202 and a hub unit 204. The hub unit 204 can include light source(s), mirror(s), capturing medium(s), filter(s), etc.

Over the course of the imaging procedure, the optical assembly 200 can be moved amongst a series of positions. For example, the optical assembly 200 may be movable between a first position 206 and a second position 208 along an arcuate path 210. By moving the optical assembly 200 between the first and second positions 206, 208 along the arcuate path 210, the retinal camera can align the lens tube 206 with the left and right eyes 212, 214 without requiring that the individual 216 readjust the position of her head during the imaging procedure.

In some embodiments, the optical assembly 200 is designed to move only along the arcuate path 210. In other embodiments, the optical assembly 200 is designed to initially move away from the left eye 212 along a substantially linear track, swing toward the right eye 214 along the arcuate path 210, and then move toward the right eye 214 along another substantially linear track. While embodiments may be described in the context of imaging the left eye before the right eye, those skilled in the art will recognize that the eyes could be imaged in any order. For example, the optical assembly 200 could be moved so that the right eye 214 is imaged before the left eye 212. As another example, the optical assembly 200 could be moved between the left and right eyes 212, 214 several times over the course of an imaging procedure.

The arcuate path 210 generally lies along a substantially horizontal plane so that optical assembly 200 moves away from the individual 216 while moving from the first position 206 to the second position 208, or vice versa. Thus, movement of the optical assembly 200 along a vertical plane may be minimal as it moves along the arcuate path 210. However, in some embodiments, the arcuate path 210 lies along a substantially vertical plane. In such embodiments, the optical assembly 200 may move upward (i.e., above the bridge of the nose) or downward (i.e., below the nostrils) as it moves from the first position 206 to the second position 208.

The retinal camera can be designed so that multiple images may be generated during a single imaging procedure without requiring the individual 216 move her head. Instead, the individual 216 may sit at the retinal camera with her forehead pressed against a flexible mask designed to envelop the left and right eyes 212, 214. Then, an ophthalmic photographer can visually align (e.g., using an eyepiece) the lens tube 202 with the left eye 212 and press a shutter release that causes an image of the retina to be captured. In some embodiments, alignment of the lens tube 202 with the left eye 212 is performed partially or entirely by the retinal camera on behalf the ophthalmic photographer. Thus, the ophthalmic photographer may not need to manually align the lens tube 202 with the left eye 212.

During an imaging operation, light can be focused via a series of lenses to form an annulus that passes through the objective lens located at the end of the lens tube 202 and onto the retina of, for example, the left eye 212. The light may be generated by a light source (e.g., a light-emitting diode) located in the hub unit 204. The series of lenses, meanwhile, may be located in the lens tube 202, hub unit 204, or any combination thereof. When the left eye 212 and the lens tube 202 are aligned, light reflected by the retina passes through the unilluminated hole in the annulus back through the objective lens located at the end of the lens tube 202.

Initially, the reflected light exiting the left eye 212 may be guided toward an eyepiece that is used by the ophthalmic photographer to assist in aligning the lens tube 202 and the left eye 212. In embodiments where alignment is performed automatically on behalf of the ophthalmic photographer, the retinal camera may not include an eyepiece for observing the reflected light. When the ophthalmic photographer determines that the lens tube 202 and the left eye 212 are aligned, she can press a shutter release that causes the reflected light to be redirected onto a capturing medium, which may be located in the hub unit 204. Examples of capturing mediums include film, digital CCDs, and CMOSs.

Then, the ophthalmic photographer can move the optical assembly 200 so that the lens tube 202 is aligned with the right eye 214 rather than the left eye 212. As further discussed below, the ophthalmic photographer may move the optical assembly 200 by interacting with an interface component, such as a lever, that is accessible along the surface of an enclosure in which the optical assembly 200 resides. Alternatively, the optical assembly 200 may be designed to automatically move responsive to determining that a quality metric for the image taken of the left eye 212 exceeds a threshold. For example, the optical assembly 200 may determine that the image taken of the left eye 212 is sufficient if resolution exceeds a threshold, blurriness falls beneath a threshold, etc.

Figure 3A:
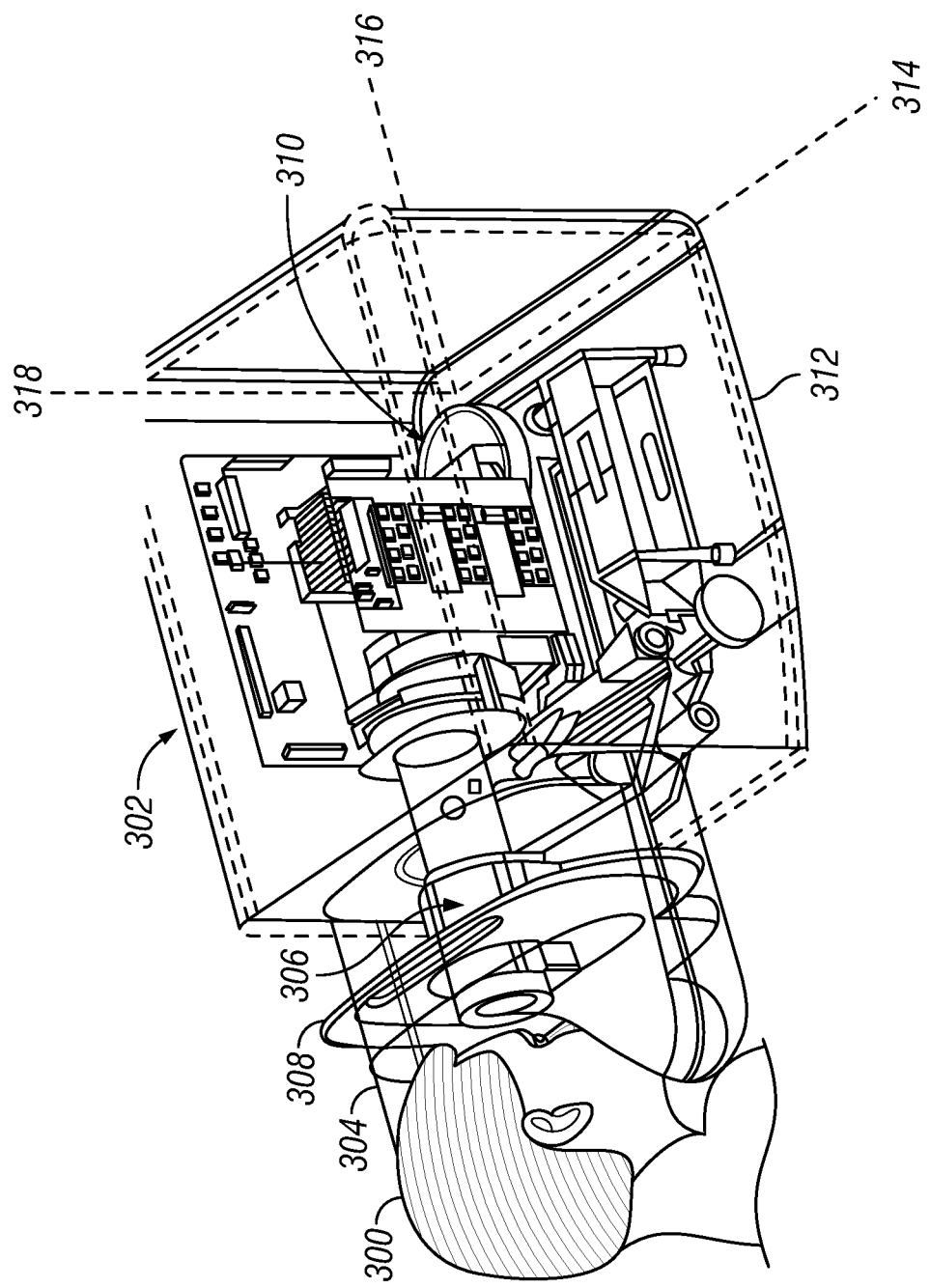
FIG. 3A depicts a scenario in which the lens tube of the optical assembly is aligned with the left eye.
Figure 3B:
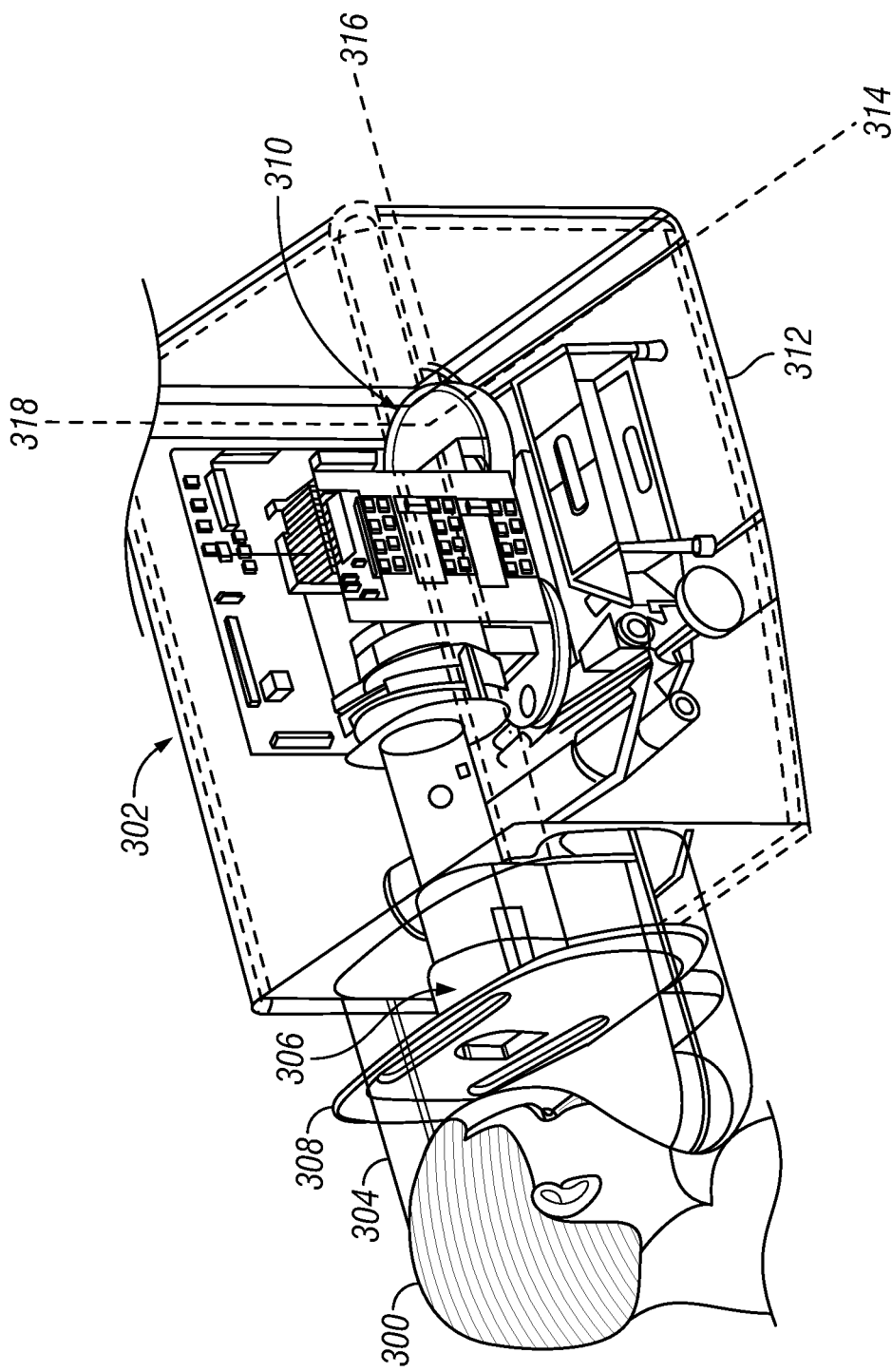
FIG. 3B illustrates how the lens tube may retract through an aperture in an occlusion plate while moving between the left and right eyes.
Figure 3C:
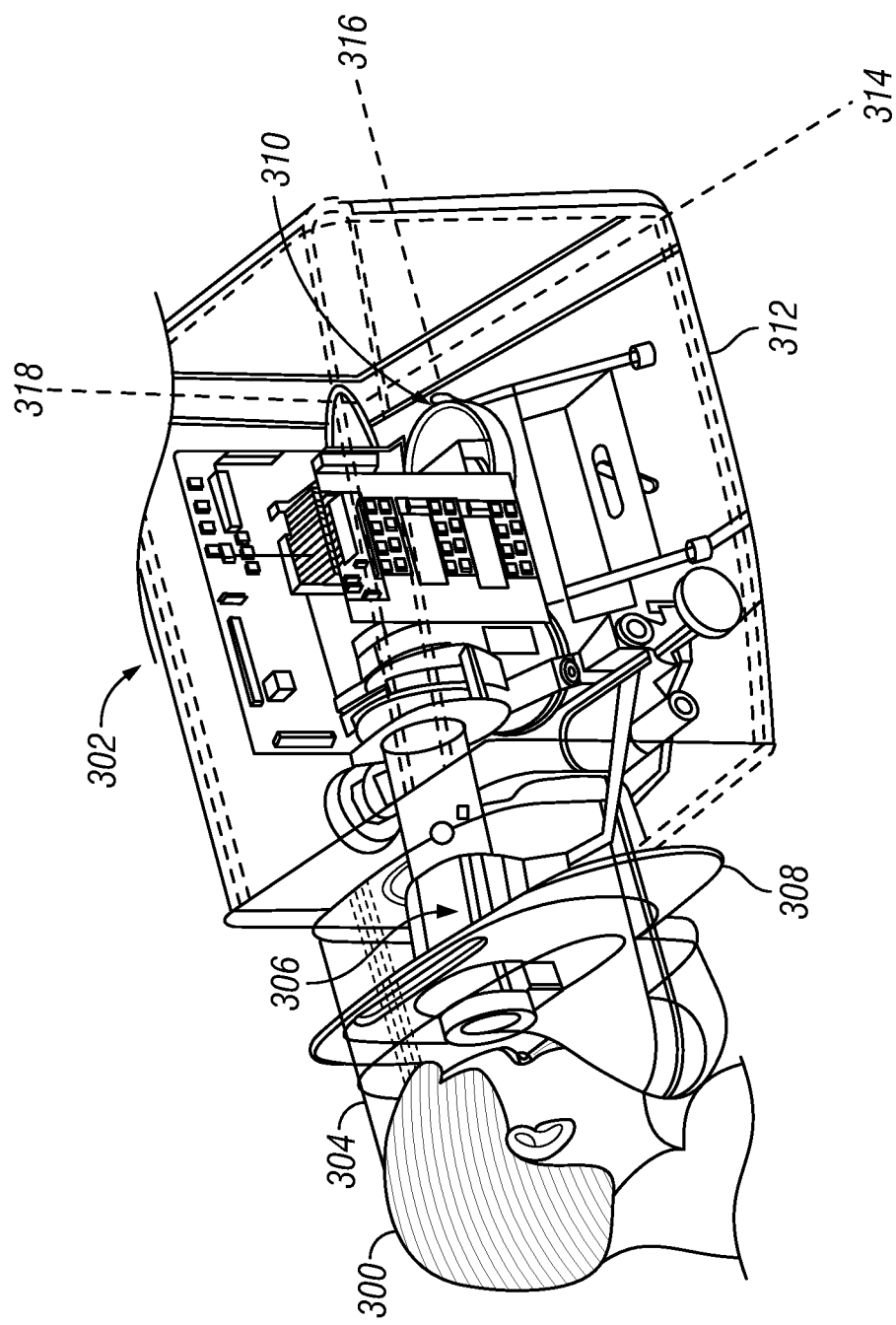
FIG. 3C depicts a scenario in which the lens tube of the optical assembly is aligned with the right eye.

FIGS. 3A-C illustrate how an optical assembly of a retinal camera 302 can shift between multiple positions during an imaging procedure so that both eyes can be imaged without requiring that an individual 300 move her head. In particular, after the individual 300 has placed her head against a flexible mask 304 designed to envelop the left and right eyes, the optical assembly of the retinal assembly 302 can be moved, either manually or automatically, between multiple positions in order to generate images of the left and right eyes. FIG. 3A depicts a scenario in which the lens tube 306 of the optical assembly is aligned with the left eye, while FIG. 3C depicts a scenario in which the lens tube 306 of the optical assembly is aligned with the right eye. FIG. 3B illustrates how the lens tube 306 may retract through an aperture in an occlusion plate 308 while moving between the left and right eyes.

Several different technologies could be employed to facilitate the movement of the optical assembly between a first position corresponding to the left eye and a second position corresponding to the right eye.

Here, for example, the optical assembly is connected to a floating plate 310 that is attached to a rod. The rod is interconnected between the floating plate 310 and an interface component accessible along the bottom surface of the enclosure 312 of the retinal camera 302. An ophthalmic photographer may be able to mechanically control the position of the optical assembly by manipulating the interface component. For example, the interface component may be movable between multiple positions corresponding to the first and second positions of the optical assembly.

In other embodiments, the retinal camera 302 includes one or more motors for moving the optical assembly. For example, the retinal camera 302 may include a first controller responsible for controlling a first motor to cause movement along the x-axis 314, a second controller responsible for controlling a second motor to cause movement along the y-axis 316, and/or a third controller responsible for controlling a third motor to cause movement along the z-axis 318. As another example, the retinal camera 302 may include a multi-axis controller responsible for separately controlling multiple motors to cause movement along the x-, y-, and/or z-axes 314, 316, 318.

Combatting Impact of Ambient Light

Historically, occluders have been used to test visual acuity by medical professionals such as ophthalmologists, orthoptists, and optometrists. For example, a pinhole occluder with one or more small holes defined therethrough may be used to focus light to temporarily remove the effects of refractive errors such as myopia. Because light will only pass through the small hole(s), the pinhole occluder can be used to distinguish visual defects caused by refractive error from other problems. As another example, a standard occluder (also referred to as a "plain occluder") may be used to occlude one eye without pressure while the other eye is being tested. Accordingly, the standard occluder may be used to ensure that each eye can be tested separately without interference due to the other eye.

As discussed above, a retinal camera may include an optical assembly that is movable between a first position and a second position. By moving the optical assembly between the first and second positions, the retinal camera can align the lens tube with the left and right eyes of an individual while clearing her nose. Thus, the left and right eyes of the individual may be imaged during a single session.

Figure 4C:
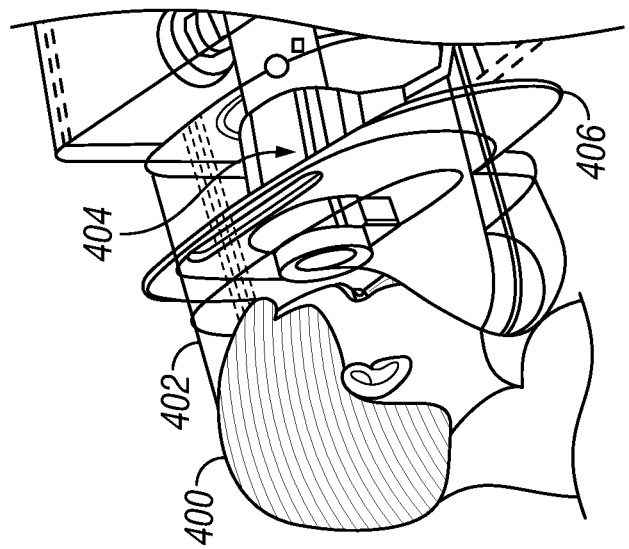
FIG. 4C depicts how the lens tube may extend through the aperture in the occlusion plate 406 when aligned with the right eye.
Figure 4B:
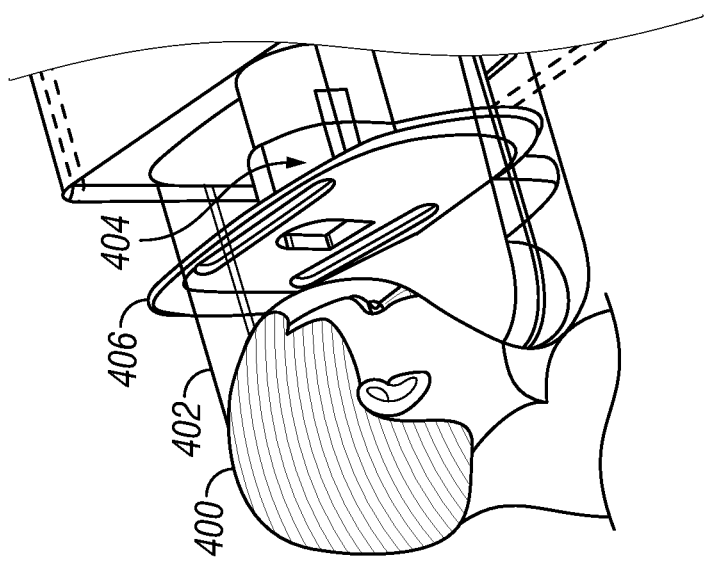
FIG. 4B illustrates how the lens tube may retract through the aperture in the occlusion plate while moving between the left and right eyes.
Figure 4A:
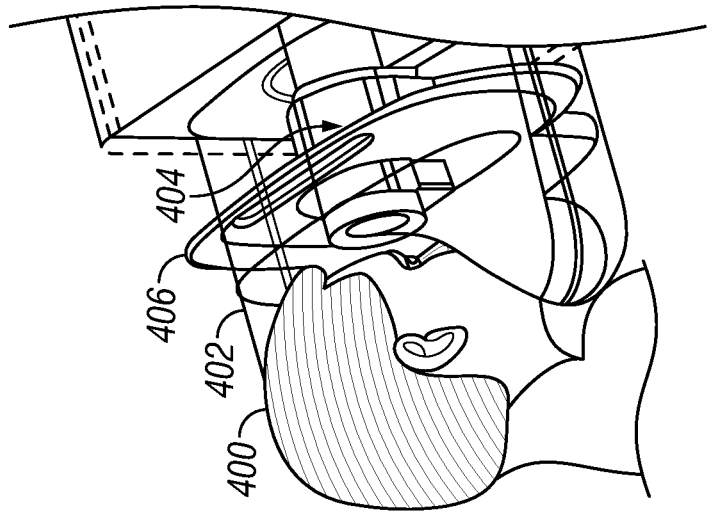
FIG. 4A depicts how the lens tube of an optical assembly may extend through an aperture in an occlusion plate when aligned with the left eye.

To promote successive imaging of the left and right eyes, the retinal camera may be designed so that the individual places the left and right eyes in a shared space. FIGS. 4A-C, for example, illustrate how an individual 400 may sit at a retinal camera with her forehead pressed against a flexible mask 402 designed to envelop the left and right eyes. Because the left and right eyes occupy a shared space, however, additional precautions may need to be taken to combat the impact of ambient light. For example, the retinal camera may include a flexible mask to combat the impact of ambient light originating from outside of the retinal camera. Examples of such ambient light is the light emitted by nearby ceiling fixtures, monitors, etc. Additionally or alternatively, the retinal camera may include an occlusion plate to combat the impact of ambient light originating from inside of the retinal camera. An example of such ambient light is the light generated by source(s) located inside the enclosure of the retinal camera. Each of these technologies is discussed in greater depth below.

FIG. 4A depicts how the lens tube 404 of an optical assembly may extend through an aperture in an occlusion plate 406 when aligned with the left eye, while FIG. 4C depicts how the lens tube 404 may extend through the aperture in the occlusion plate 406 when aligned with the right eye. FIG. 4B illustrates how the lens tube 404 may retract through the aperture in the occlusion plate 406 while moving between the left and right eyes.

As shown in FIGS. 4A-C, the flexible mask 402 may include slots along opposing sides in order to accommodate the occlusion plate 406 as it shifts along a substantially vertical plane in conjunction with the optical assembly. In FIG. 4A, for example, a portion of the occlusion plate 406 extends through the slot on the far side of the flexible mask 402. To prevent ambient light from leaking into the cavity defined by the flexible mask 402, the occlusion plate 406 may not retract through the slot on the near side of the flexible mask 402. Instead, the occlusion plate 406 may be designed and installed such that the slots in the flexible mask 402 are always occupied. As shown in FIG. 4C, when the occlusion plate 406 shifts in conjunction with the optical assembly, another portion of the occlusion plate 406 may extend through the slot on the near side of the flexible mask 402.

As further discussed below with respect to FIGS. 5A-B, the flexible mask 402 may be designed to envelop the left and right eyes of the individual 400 without any components interrupting the cavity defined by the interior surface of the flexible mask 402. Thus, the flexible mask 402 may envelop the eyes much like a head-mounted display. Because the left and right eyes occupy a shared space, the occlusion plate 406 may be necessary to ensure that whichever eye is not being imaged is exposed to as little light as possible. During an imaging operation, the occlusion plate 406 may have a similar effect as the occlusion instruments (also referred to as "occluders" or "occluder spoons") used during conventional eye examinations.

In some embodiments, the occlusion plate 406 has a planar surface that is substantially parallel with the vertical plane. In other embodiments, the occlusion plate 406 has a non-planar surface. For example, the occlusion plate 406 may include geometric features, such as protrusions or depressions, that reduce the amount of light that is observable by whichever eye is not being imaged.

The occlusion plate 406 can be comprised of one or more materials that are opaque to visible light. Examples of such materials include plastics, woods, and metals. However, the occlusion plate 406 is normally comprised of non-metallic material(s) in order to avoid reflections of light. For example, the occlusion plate 406 may be comprised of black medical-grade plastic with smoothly finished edges to keep the cavity defined by the flexible mask 402 as dark as possible.

In some embodiments, the occlusion plate 406 is mechanically coupled to the lens tube 404, the interface component used to alter the position of the lens tube 404, or another component of the optical assembly. For example, the occlusion plate 406 may be connected to a mechanical gasket in the shape of a torus through which the distal end of the lens tube 404 extends/retracts as it moves from one position to another, and the mechanical gasket may be slidably mounted on the lens tube 404. As another example, the occlusion plate 406 may be connected to a floating plate, and the floating plate may be attached to a rod connected to the interface component.

In other embodiments, the occlusion plate 406 moves independently but in conjunction with the lens tube 404. For example, in embodiments where the lens tube 404 is moved between various positions by motor(s), another motor may be responsible for shifting the occlusion plate 406. Generally, movement of the occlusion plate 406 is confined to a substantially vertical plane. In FIGS. 4A-C, for example, the occlusion plate 406 shifts from the leftmost position to the rightmost position while remaining the same distance away from the individual 400. Planar movement may be facilitated by a structural feature, such as a mechanical track, installed in the flexible mask 402 (or at the interface between the flexible mask 402 and enclosure).

Figure 5A:
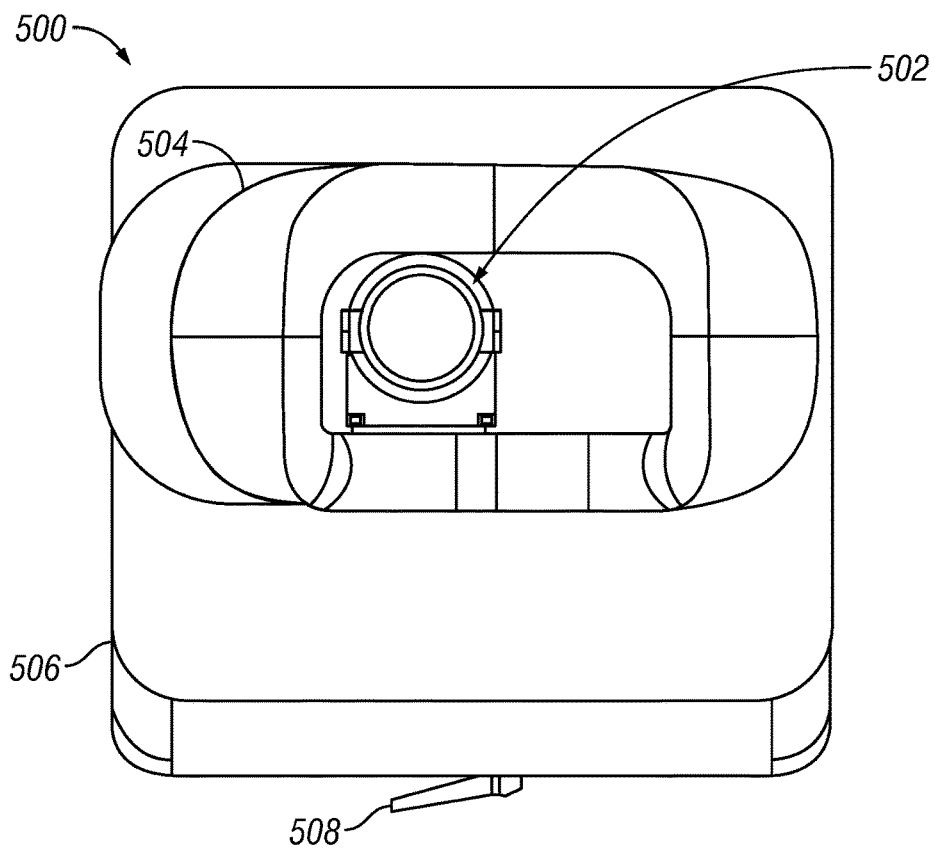
FIG. 5A illustrates how the lens tube of a retinal camera can be moved into a first position aligned with a left eye within a cavity defined by the interior surface of a flexible mask.
Figure 5B:
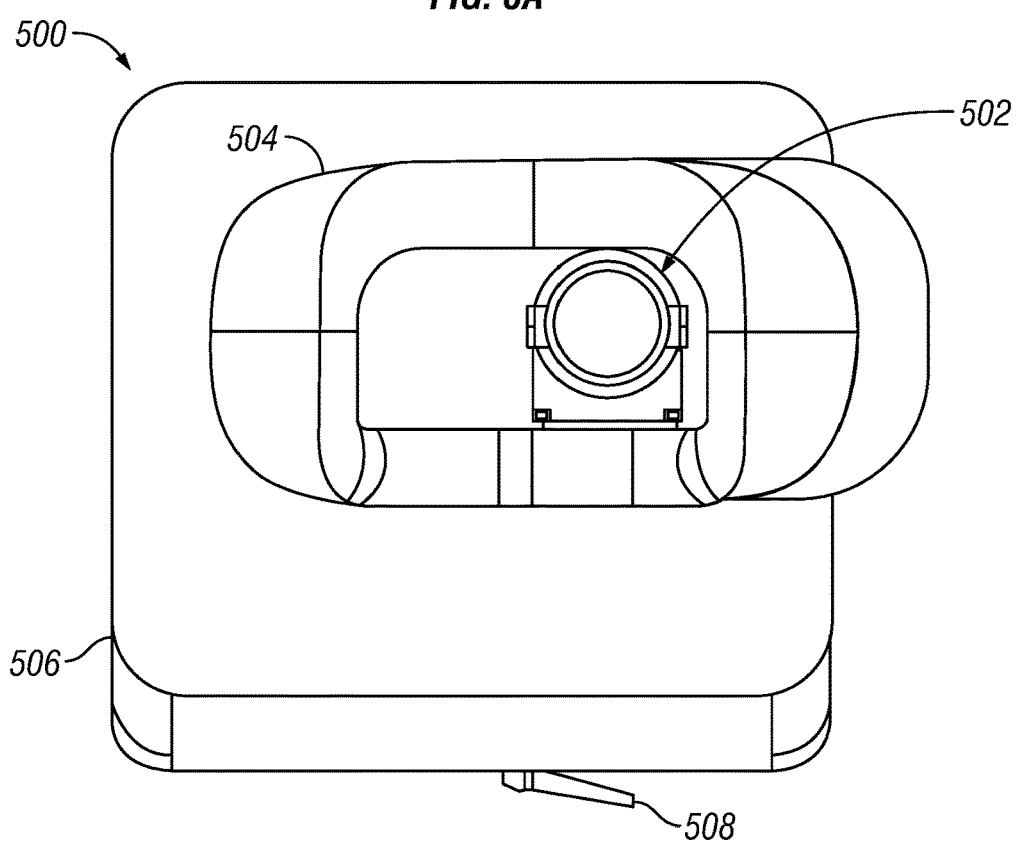
FIG. 5B illustrates how the lens tube of a retinal camera can be moved into a second position aligned with a right eye within the cavity defined by the interior surface of the flexible mask.

FIGS. 5A-B illustrate how the lens tube 502 of a retinal camera 500 can be moved from a first position to a second position within a cavity defined by the interior surface of a flexible mask 504. As discussed above, an individual may place her head against the flexible mask 504 that is connected to an enclosure 506. The flexible mask 504 may be designed and connected to the enclosure 506 in such a manner to facilitate alignment of the left and right eyes with the first and second positions of the lens tube 502. For example, the flexible mask 504 may include a notch along its lower side for accommodating the bridge of the nose.

The flexible mask 504 may be designed to envelop the left and right eyes of the individual. The field of vision of whichever eye is presently being imaged may be almost entirely occupied by the objective lens, though the lens tube, occlusion plate, and interior surface of the flexible mask 504 may be partially visible. The field of vision of whichever eye is not presently being imaged may be almost entirely occupied by the lens tube, occlusion plate, and interior surface of the flexible mask 504. Accordingly, these components may be comprised of opaque material(s), coated in opaque paint, etc. For example, the lens tube, occlusion plate, and interior surface of the flexible mask 504 may be comprised of, or coated with, black materials.

The flexible mask 504 can be comprised of rubber, silicone foam, or some other conformable material. For example, the flexible mask 502 may be comprised of a medical-grade foam that is soft, breathable, and resistant to liquids. When the individual presses her face against the flexible mask 502, the flexible mask 502 may conform to her face to ensure that the left and right eyes are substantially shielded from ambient light.

When an ophthalmic photographer determines that the lens tube 502 is aligned with the left eye, she can press a shutter release that causes light reflected by the retina to be redirected onto a capturing medium located in the enclosure 506. Then, the ophthalmic photographer can move the lens tube 502 so that it is aligned with the right eye rather than the left eye. The ophthalmic photographer may move the lens tube 502 by interacting with an interface component 508 that is accessible along the surface of the enclosure 506. Here, the interface component 508 is a lever that allows the ophthalmic photographer to move the lens tube 502 between multiple predefined positions. However, the interface component 508 may be designed to allow the ophthalmic photographer to freely move the lens tube 502 along a predefined path (e.g., without any predefined positions). Other examples of interface components include knobs, switches, etc.

As discussed above, the lens tube 502 may move from a first position aligned with the left eye to a second position aligned with the right eye along an arcuate path that causes the lens tube 502 to move away from the individual while moving between the first and second positions. In such embodiments, the movement may occur along a substantially horizontal plane. Thus, the lens tube 502 may remain in the cavity defined by the interior surface of the flexible mask 504 throughout the imaging procedure, though the lens tube 502 may move closer/further to the individual as it changes position.

As shown in FIGS. 5A-B, the flexible mask 504 may be designed to accommodate the face of the individual undergoing examination. For example, the superior side of the flexible mask 504 may include a slight depression to accommodate the forehead. Similarly, the inferior side of the flexible mask 504 may be designed to accommodate the nose, cheekbones, etc. For example, the interior side of the flexible mask 504 includes a notch sized to fit the bridge of the nose. Together, the superior and interior sides of the flexible mask 504 may be designed to promote alignment of the left and right eyes with the positions to which the lens tube 502 can be moved.

Controlling Movement of the Optical Assembly

Figure 6A:
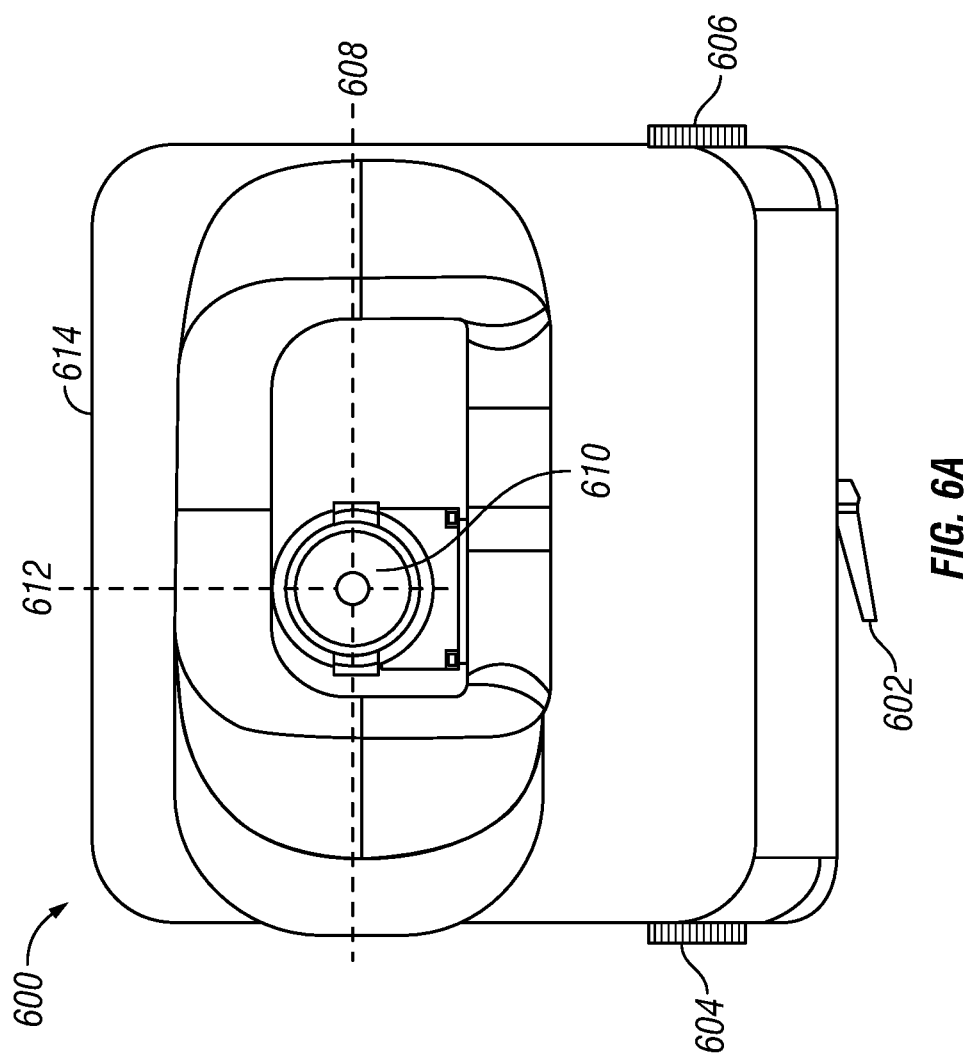
FIG. 6A includes a front view of a retinal camera that includes a first interface component for switching the optical assembly between the left and right eyes, a second interface component for adjusting the position of the optical assembly along the x-axis, and a third interface component for adjusting the position of the optical assembly along the y-axis.
Figure 6B:
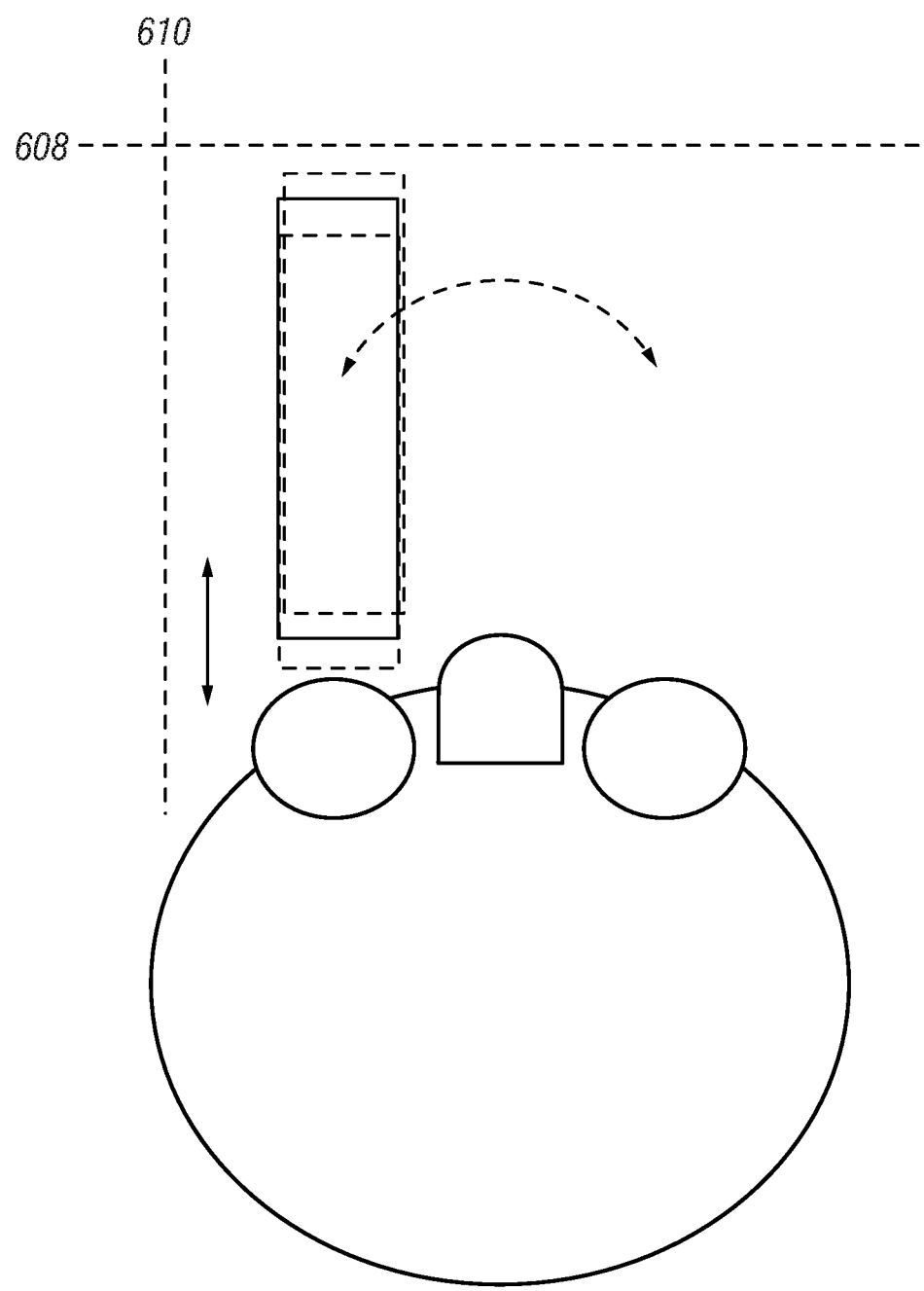
FIG. 6B includes a top view of the retinal camera that illustrates how the lens tube can be moved along the x- and y-axes.

To control the movement of the optical assembly (and thus the lens tube), an ophthalmic photographer may control one or more interface components accessible along the surface of an enclosure 614. FIG. 6A includes a front view of a retinal camera 600 that includes a first interface component 602 for switching the optical assembly between the left and right eyes, a second interface component 604 for adjusting the position of the optical assembly along the x-axis 608, and a third interface component 606 for adjusting the position of the optical assembly along the y-axis 610. In some embodiments, the retinal camera 600 further includes a fourth interface component for adjusting the position of the optical assembly along the z-axis 612. FIG. 6B includes a top view of the retinal camera 600 that illustrates how the lens tube can be moved along the x- and y-axes 608, 610.

Each interface component may be a separately manipulable mechanical component. Here, for example, the first interface component 602 is a lever located on the bottom side of the enclosure 614, and the second and third interface components 604, 606 are knobs located on opposite sides of the enclosure 614. Note, however, that the interface components could be located in other positions. For example, all interface components could be located on a single side of the enclosure 614. In some embodiments, the ophthalmic photographer controls the lens tube using a single joystick. Thus, the joystick may replace the first interface component 602, second interface component 604, and/or third interface component 606.

In some embodiments, the second and third interface components 604, 606 provide different adjustments in different degrees of freedom. For example, the second interface mechanism 604 may be an indexing knob connected to a first differential screw with a first pitch, and the third interface mechanism 606 may be an indexing knob that is connected to a second differential screw with a second pitch. The "pitch" of a differential screw refers to the distance from the crest of one thread to the crest of the next thread (i.e., the distance the differential screw advances when it turns one revolution). The pitch controls how far each differential screw will advance when turned a single revolution (or a fraction thereof). For instance, each revolution of the second interface mechanism 604 (and thus the first differential screw) may cause the lens tube to move 2.5 millimeters (mm) along the x-axis 608, while each revolution of the third interface mechanism 606 (and thus the second differential screw) may cause the lens tube to move 5.0 mm along the y-axis 610. The second and third interface mechanisms 604, 606 may be designed so that the ophthalmic photographer can control the lens tube with greater precision. For instance, the second interface mechanism 604 may be designed so that each revolution is comprised of five equal segments, and each segment may correspond to movement along the x-axis 608 of approximately 0.5 mm. Similarly, the third interface mechanism 606 may be designed so that each revolution is comprised of five equal segments, and each segment may correspond to movement along the y-axis 610 of approximately 1.0 mm.

In other embodiments, the second and third interface components 604, 606 provide roughly equal adjustments in different degrees of freedom. For example, the second and third interface mechanisms 604, 606 may be indexing knobs that are connected to identical differential screws. In such embodiments, each revolution of the second and third interface mechanisms 604, 606 may cause the lens tube to move identical amounts along the x- and y-axes 608, 610.

The first, second, and/or third interface components 602, 604, 606 may be designed to permit bidirectional movement. Here, for example, the first interface component 602 is a lever that can be shifted leftward to move the lens tube into alignment with the left eye and rightward to move the lens tube into alignment with the right eye. Similarly, the second and third interface components 604, 606 are indexing knobs that cause movement in one direction when turned clockwise and the other direction when turned counterclockwise.

Moreover, each interface component may control movement of the lens tube independent of the other interface components. For example, the first interface component 602 may control movement as facilitated by a floating plate, while the second and third interface components 604, 606 may control movement as facilitated by differential screws, motors, racks and pinions, etc. For example, the second interface component 604 may be connected to a first circular gear that engages a first linear gear, which operates to translate rotational motion into linear motion along the x-axis 608, and the third interface component 606 may be connected to a second circular gear that engages a second linear gear, which operates to translate rotational motion into linear motion along the y-axis 610. As noted above, the first and second linear gears may provide similar or different adjustments in different degrees of freedom.

Methodologies for Multi-Stage Retinal Imaging

Figure 7:
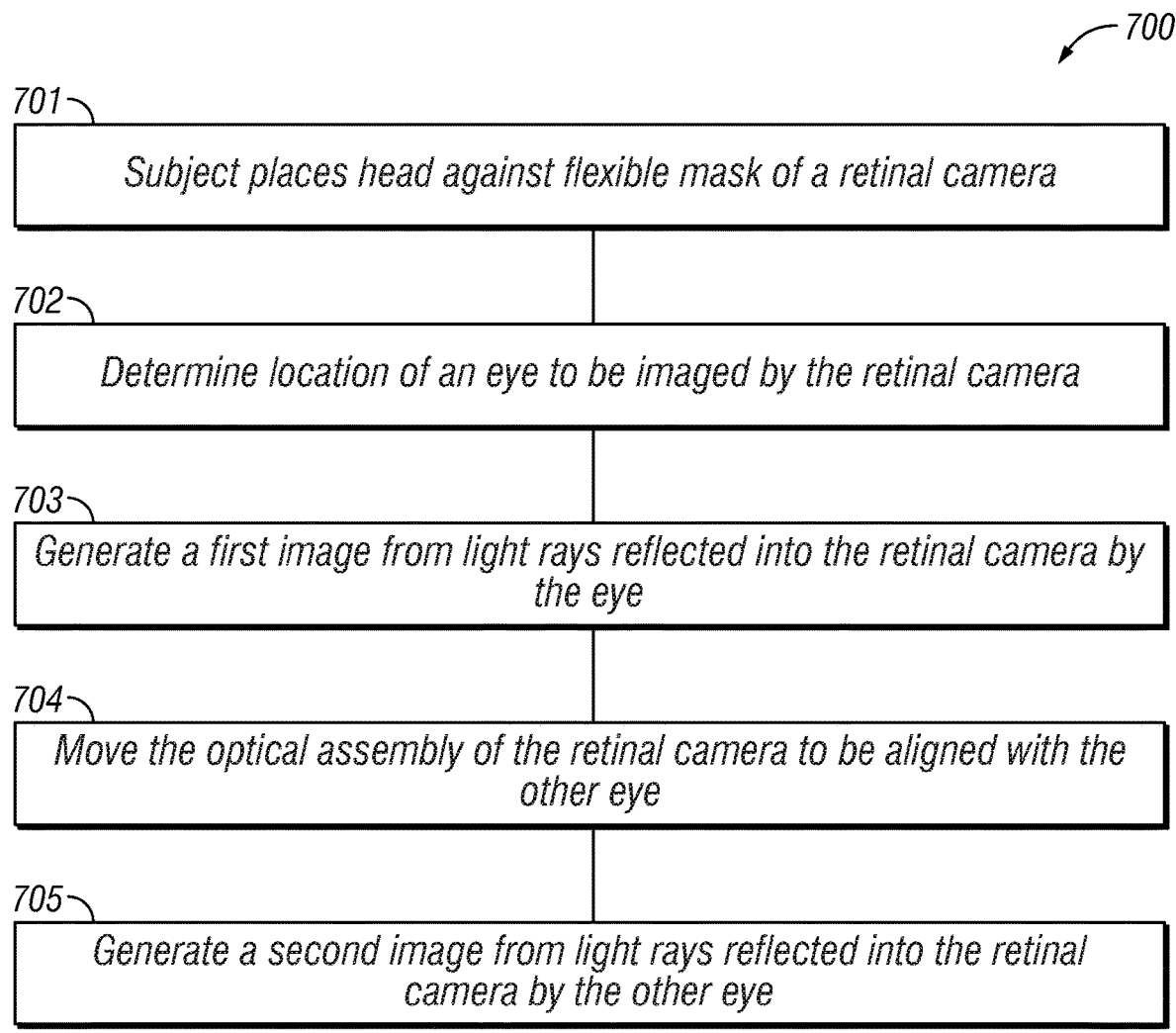
FIG. 7 depicts a flow diagram of a process for manually shifting an optical assembly housed within a retinal camera in order to generate images of the left and right eyes during an imaging procedure.

FIG. 7 depicts a flow diagram of a process 700 for manually shifting an optical assembly housed within a retinal camera in order to generate images of the left and right eyes during an imaging procedure. Initially, a subject plates her head against the flexible mask of a retinal camera (step 701). As noted above, other structural features may facilitate alignment of the head with the retinal camera. For example, the subject may also place her chin within a chin rest located beneath the flexible mask and/or press her forehead against a bar located above the flexible mask.

Then, the location of the eye being imaged by the optical assembly of the retinal camera is determined (step 702). In some embodiments, an ophthalmic photographer determines the location of the eye by observing light reflected by the retina through an eyepiece. In other embodiments, the retina camera determines the location of the eye on behalf of the ophthalmic photographer. For example, infrared light source(s) may be configured to project infrared beam(s) along the visible light illumination path of the retinal camera. Because the iris will generally not constrict when illuminated by infrared light, a live view of the retina can be captured by the retina camera and used to establish the position of the eye. As another example, the retinal camera may capture images with the optical assembly located at different positions. Image processing algorithm(s) can then be applied to the images to determine whether the retina has been captured in any of the images.

The retinal camera can then generate a first image from light rays reflected through the lens tube into the retinal camera by the eye (step 703). Such action may be performed responsive to determining that the lens tube has been aligned with the eye, either manually or automatically. The retinal camera may be prompted to generate the image by an ophthalmic photographer pressing a shutter release that causes the image to be captured.

Thereafter, the ophthalmic photographer can move the optical assembly of the retinal camera to be aligned with the other eye (step 704). To accomplish this, the ophthalmic photographer may interact with an interface component, such as a lever, switch, or knob, accessible along the exterior surface of the retinal camera. As shown in FIG. 6A, for example, the ophthalmic photographer could interact with a lever that can be shifted leftward to move the lens tube into alignment with the left eye and rightward to move the lens tube into alignment with the right eye.

The retinal camera can then generate a second image from light rays reflected through the lens tube into the retinal camera by the other eye (step 705). Again, such action may be performed responsive to determining that the lens tube has been aligned with the other eye, either manually or automatically. The retinal camera may be prompted to generate the second image by the ophthalmic photographer pressing the shutter release.

Figure 8:
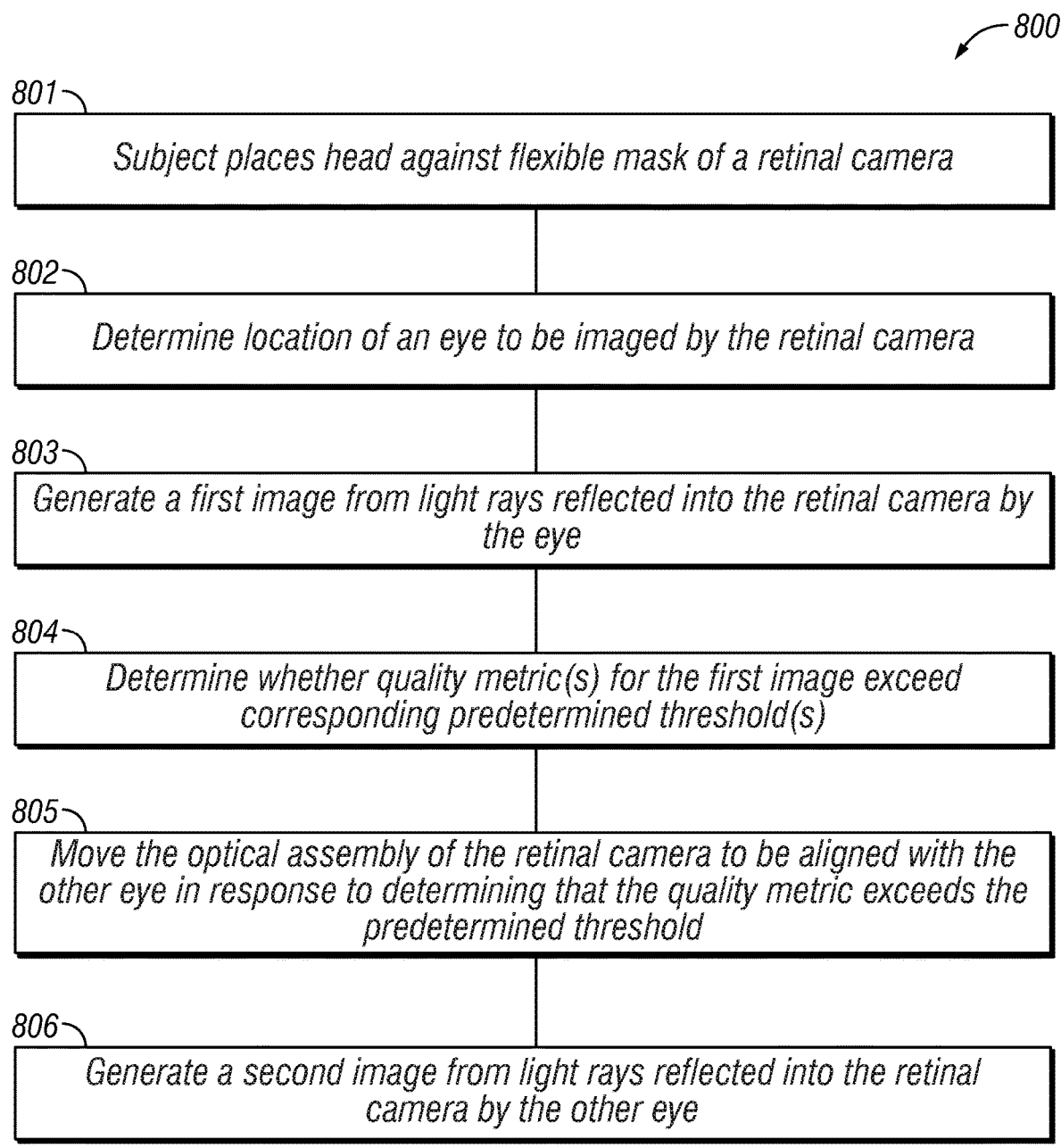
FIG. 8 depicts a flow diagram of a process for automatically shifting an optical assembly housed within a retinal camera in order to generate images of the left and right eyes during an imaging procedure.

FIG. 8 depicts a flow diagram of a process 800 for automatically shifting an optical assembly housed within a retinal camera in order to generate images of the left and right eyes during an imaging procedure. Steps 801-803 of process 800 may be substantially similar to steps 701-703 of process 700. Here, however, the retinal camera determines whether quality metric(s) for the first image exceed corresponding predetermined threshold(s) (step 804). For example, a processor may examine the pixel data of the first image to determine whether its resolution exceeds a threshold, whether its blurriness falls beneath a threshold, whether its contrast exceeds a threshold, etc. In some embodiments, the processor is programmed to apply algorithms to generate a separate quality metric for each criterion under consideration. For instance, the processor may generate a first quality metric indicative of resolution, a second quality metric indicative of blurriness, etc. Alternatively, the processor may only generate a quality metric for a single criterion (e.g., blurriness). Then, the processor can determine whether quality of the first image is sufficient by comparing these quality metric(s) to predetermined threshold(s). In some embodiments the processor is housed within the retinal camera, while in other embodiments the processor is housed within an electronic device that is communicatively coupled to the retinal camera.

Responsive to determining that the quality metric(s) exceed the corresponding predetermined threshold(s), the retinal camera can automatically move the optical assembly to be aligned with the other eye (step 805). For example, the retinal camera may include one or more motors for moving the optical assembly on behalf of the ophthalmic photographer. As discussed above with respect to FIGS. 3A-C, the retinal camera may include a first controller responsible for controlling a first motor to cause movement along the x-axis, a second controller responsible for controlling a second motor to cause movement along the y-axis, and/or a third controller responsible for controlling a third motor to cause movement along the z-axis. Alternatively, the retinal camera may include a multi-axis controller responsible for separately controlling multiple motors to cause movement along the x-, y-, and/or z-axes.

Movement of the optical assembly may be controlled based on, for example, the content of images generated by the retinal camera. For instance, the retinal camera may shift the optical assembly from a first position proximate to the left eye to a second position proximate to the right eye along an arcuate path. Then, the retinal camera may make minor adjustments to the position of the optical assembly after it has been moved into the second position based on the content of images generated by the retinal camera. Thus, the retinal camera may generate a series of images with the optical assembly located in different positions and then reposition the optical assembly based on which image(s), if any, include the retina. Step 806 of process 800 may be substantially similar to step 705 of process 700.

Figure 9:
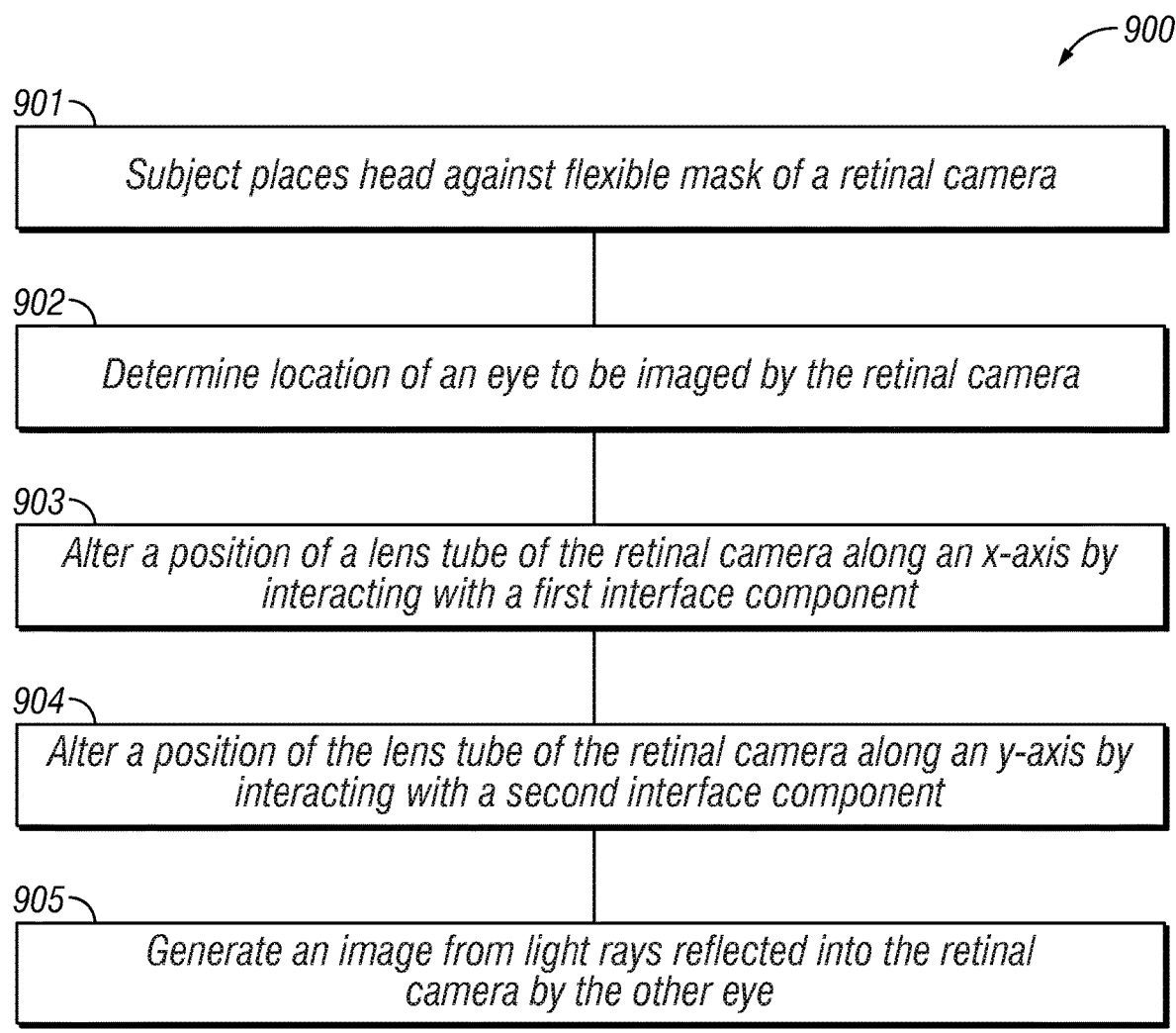
FIG. 9 depicts a flow diagram of a process for altering the position of an optical assembly located proximate to an eye of a subject before an imaging procedure.

FIG. 9 depicts a flow diagram of a process 900 for altering the position of an optical assembly located proximate to an eye of a subject before an imaging procedure. Steps 901-902 of process 900 may be substantially similar to steps 701-702 of process 700. Here, however, the ophthalmic photographer has opted to manually alter the position of the optical assembly with respect to the eye.

After determining the location of the eye, the ophthalmic photographer may opt to alter the position of an objective lens installed within a lens tube along an x-axis orthogonal to the length of the lens tube or a y-axis parallel to the length of the lens tube. For example, the ophthalmic photographer may alter the position of the lens tube along the x-axis by interacting with a first interface component (step 903). Additionally or alternatively, the ophthalmic photographer may alter the position of the lens tube along the y-axis by interacting with a second interface component (step 904). As shown in FIG. 6A, the first and second interface components may be arranged along opposite sides of the retinal camera so that the ophthalmic photographer can readily interact with both interface components, for example, while observing light reflected by the retina through an eyepiece. Thus, the ophthalmic photographer may be able to alter the position of the lens tube along the x- and y-axes either successively or simultaneously. In some embodiments, the first and second interface components are the same interface component. For example, the ophthalmic photographer may alter the position of the lens tube along the x- and y-axes using a single joystick.

Then, the retinal camera can generate an image from light rays reflected through the lens tube into the retinal camera by the eye (step 905). For example, the retinal camera may be prompted to generate the image by the ophthalmic photographer pressing a shutter release after determining that the lens tube and eye are aligned.

These steps may be performed in various sequences and combinations. For example, the ophthalmic photographer may alter the position of the lens tube of the retinal camera along the y-axis before altering its position along the x-axis. That is, step 904 of process 900 may be performed before, or in conjunction with, step 903 of process 900. As another example, steps 903-904 of process 900 may be performed immediately before step 703 of process 700, step 705 of process 700, step 803 of process 800, and/or step 806 of process 800.

Other steps may also be included in some embodiments. For example, in some embodiments, the retinal camera may guide the ophthalmic photographer in aligning the lens tube with the eye. This may be accomplished by providing notifications (e.g., audible, visual, or tactile notifications) intended to facilitate alignment of these objects. As another example, the retinal camera may be configured to automatically upload images to a network-accessible platform programmed to analyze the images, store the images in a profile associated with the subject, etc.

Processing System

Figure 10:
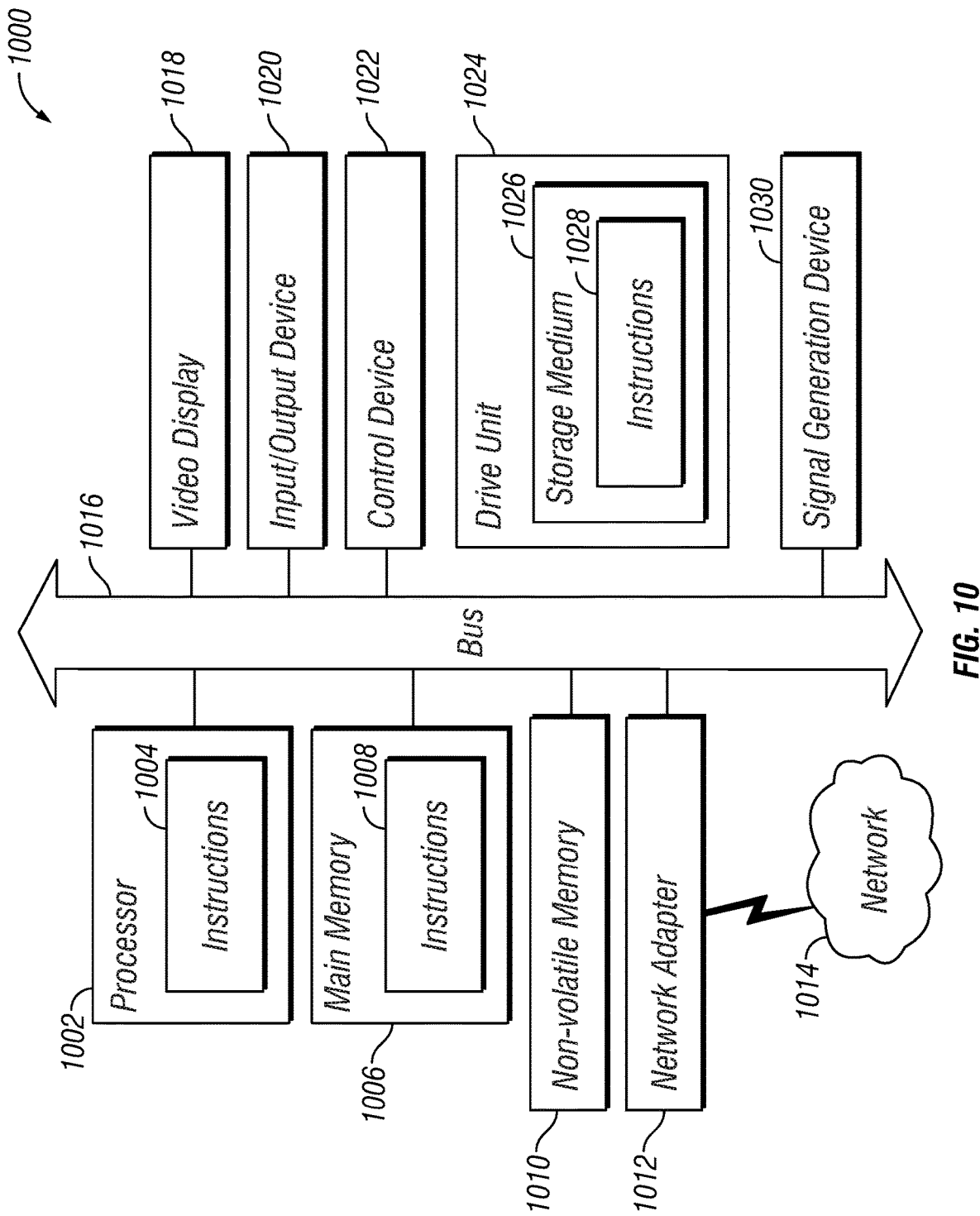
FIG. 10 is a block diagram illustrating an example of a processing system 1000 in which at least some operations described herein can be implemented.

FIG. 10 is a block diagram illustrating an example of a processing system 1000 in which at least some operations described herein can be implemented. For example, some components of the processing system 1000 may be hosted on a retinal camera (e.g., retinal camera 302 of FIG. 3), while other components of the processing system 1000 may be hosted on a computing device that is communicatively coupled to the retinal camera. The computing device may be connected to the retinal camera via a wired channel or a wireless channel.

The processing system 1000 may include one or more central processing units ("processors") 1002, main memory 1006, non-volatile memory 1010, network adapter 1012 (e.g., network interface), video display 1018, input/output devices 1020, control device 1022 (e.g., keyboard and pointing devices), drive unit 1024 including a storage medium 1026, and signal generation device 1030 that are communicatively connected to a bus 1016. The bus 1016 is illustrated as an abstraction that represents one or more physical buses and/or point-to-point connections that are connected by appropriate bridges, adapters, or controllers. The bus 1016, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1000 may share a similar computer processor architecture as that of a desktop computer, tablet computer, personal digital assistant (PDA), mobile phone, game console, music player, wearable electronic device (e.g., a watch or fitness band), network-connected ("smart") device (e.g., a television or home assistant device), virtual/augmented reality system (e.g., a head-mounted display), or another electronic device capable of executing a set of instructions (sequential or otherwise) that specify action(s) to be taken by the processing system 1000.

While the main memory 1006, non-volatile memory 1010, and storage medium 1026 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1028. The term "machine-readable medium" and "storage medium" shall also be taken to include any medium that is capable of storing, encoding, or carrying a set of instructions for execution by the processing system 1000.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1004, 1008, 1028) set at various times in various memory and storage devices in a computing device. When read and executed by the one or more processors 1002, the instruction(s) cause the processing system 1000 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1010, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1012 enables the processing system 1000 to mediate data in a network 1014 with an entity that is external to the processing system 1000 through any communication protocol supported by the processing system 1000 and the external entity. The network adapter 1012 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1012 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. An imaging apparatus comprising:
   an optical assembly movable between a first position and a second position along an arcuate path,
     wherein the optical assembly includes:
       a light source configured to emit light therefrom into an eye for illumination of a retina during an imaging procedure,
       an objective lens configured to collect reflected light so as to image the retina, and
       a lens tube configured to direct the reflected light toward a capturing medium;
   an enclosure in which at least a portion of the optical assembly is housed;
   a first interface component accessible along an exterior surface of the enclosure for moving the optical assembly between the first and second positions; and
   a mask connected to the enclosure in such a manner to facilitate alignment of a left eye with the first position and a right eye with the second position,
     wherein the mask is comprised of a flexible material configured to confirm to a face pressed against the mask to prevent ambient light from entering a cavity defined by an interior surface of the mask.

2. The imaging apparatus of claim 1,
   wherein the arcuate path is defined along a horizontal plane, and
   wherein movement of the optical assembly along a vertical plane is substantially zero as the optical assembly moves along the arcuate path.

3. The imaging apparatus of claim 1, wherein the reflected light is light reflected off of the retina that has passed through the objective lens.

4. The imaging apparatus of claim 1, further comprising:
   a second interface component for moving the optical assembly along a vertical plane; and
   a third interface component for moving the optical assembly along a horizontal plane.

5. The imaging apparatus of claim 4, wherein the second and third interface components are positioned along opposite sides of the enclosure.

6. The imaging apparatus of claim 4, wherein the first, second, and third interface components are separately manipulable mechanical components.

7. The imaging apparatus of claim 1, further comprising:
   an occlusion plate having an aperture through which the objective lens extends when the optical assembly is located in the first and second positions.

8. The imaging apparatus of claim 7, wherein the mask includes a pair of slots for accommodating the occlusion plate.

9. The imaging apparatus of claim 8,
   wherein a first portion of the occlusion plate extends through a first slot of the pair of slots into an ambient environment when the optical assembly is located in the first position, and
   wherein a second portion of the occlusion plate extends through a second slot of the pair of slots into the ambient environment when the optical assembly is located in the second position.

10. The imaging apparatus of claim 7, wherein the occlusion plate is movable along a linear path in conjunction with the arcuate movement of the optical assembly.

11. The imaging apparatus of claim 7, wherein the objective lens retracts through the aperture in the occlusion plate as the optical assembly moves between the first and second positions.

12. An imaging apparatus comprising:
an optical assembly movable between a first position and a second position along an arcuate path,
wherein the optical assembly includes:
a light source configured to emit light therefrom into an eye for illumination of a retina during an imaging procedure,
an objective lens configured to collect reflected light so as to image the retina, and
a lens tube configured to direct the reflected light toward a capturing medium;
an enclosure in which at least a portion of the optical assembly is housed;
a first interface component accessible along an exterior surface of the enclosure for moving the optical assembly between the first and second positions;
an occlusion plate having an aperture through which the objective lens extends when the optical assembly is located in the first and second positions; and
a mask connected to the enclosure in such a manner to facilitate alignment of a left eye with the first position and a right eye with the second position,
wherein the mask includes a pair of slots for accommodating the occlusion plate,
wherein a first portion of the occlusion plate extends through a first slot of the pair of slots into an ambient environment when the optical assembly is located in the first position, and
wherein a second portion of the occlusion plate extends through a second slot of the pair of slots into the ambient environment when the optical assembly is located in the second position.

13. The imaging apparatus of claim 12,
wherein the arcuate path is defined along a horizontal plane, and
wherein movement of the optical assembly along a vertical plane is substantially zero as the optical assembly moves along the arcuate path.

14. The imaging apparatus of claim 12, wherein the reflected light is light reflected off of the retina that has passed through the objective lens.

15. The imaging apparatus of claim 12, further comprising:
a second interface component for moving the optical assembly along a vertical plane; and
a third interface component for moving the optical assembly along a horizontal plane.

16. The imaging apparatus of claim 15, wherein the second and third interface components are positioned along opposite sides of the enclosure.

17. The imaging apparatus of claim 15, wherein the first, second, and third interface components are separately manipulable mechanical components.

18. The imaging apparatus of claim 12, wherein the occlusion plate is movable along a linear path in conjunction with the arcuate movement of the optical assembly.

19. The imaging apparatus of claim 12, wherein the objective lens retracts through the aperture in the occlusion plate as the optical assembly moves between the first and second positions.

* * * * *